(12) United States Patent
Gregan et al.

(10) Patent No.: US 10,779,805 B2
(45) Date of Patent: Sep. 22, 2020

(54) WIRE GUIDED DEVICE

(71) Applicant: UNITED STATES ENDOSCOPY GROUP, INC., Mentor, OH (US)

(72) Inventors: Darren C. Gregan, Auburn Township, OH (US); Scott Haack, Chardon, OH (US); Alex Uspenski, Chardon, OH (US); Sarah Insull, Painesville, OH (US); Joseph Michelini, Painesville, OH (US); Cindy Ranallo, Eastlake, OH (US); Gerald Chiappone, Painesville, OH (US); Joseph Mrva, Kirtland, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 76 days.

(21) Appl. No.: 16/138,227

(22) Filed: Sep. 21, 2018

(65) Prior Publication Data

US 2019/0083072 A1 Mar. 21, 2019

Related U.S. Application Data

(60) Provisional application No. 62/561,439, filed on Sep. 21, 2017.

(51) Int. Cl.
*A61B 10/04* (2006.01)
*A61B 10/06* (2006.01)
(Continued)

(52) U.S. Cl.
CPC .............. *A61B 10/04* (2013.01); *A61B 10/06* (2013.01); *A61B 17/29* (2013.01); *A61B 2017/22039* (2013.01)

(58) Field of Classification Search
CPC . A61B 10/06; A61B 17/29; A61B 17/320016; A61B 17/3417; A61B 17/28;
(Continued)

(56) References Cited

U.S. PATENT DOCUMENTS 3,537,456 A * 11/1970 Harautuneian ............ A61F 5/44
604/326
2005/0054946 A1    3/2005 Krzyzanowski
(Continued)

FOREIGN PATENT DOCUMENTS

JP     2002119514 A  *  4/2002
JP     2002119514 A     4/2002

OTHER PUBLICATIONS

English Translation of JP 2002119514 from Espacenet (Year: 2002).*
(Continued)

*Primary Examiner* — Gregory A Anderson
*Assistant Examiner* — Alyssa M Keane
(74) *Attorney, Agent, or Firm* — Calfee, Halter & Griswold, LLP (57) ABSTRACT

The present subject matter discloses a wire guided device, including a sheath, a working assembly, and a wire guide. The working assembly includes a working portion, configured to contact an intended tissue, and a connector, connecting the working portion and the sheath. The wire guide is disposed at and connected to the working assembly. The wire guide is configured to allow a guide wire to pass through, wherein the wire guide is disposed at a predetermined distance from a distal end of the working assembly. The wire guide and the guide wire do not interfere with an operation of the working portion.

16 Claims, 8 Drawing Sheets

(51) Int. Cl.
*A61B 17/29* (2006.01)
*A61B 17/22* (2006.01)

(58) Field of Classification Search
CPC ...... A61B 17/2909; A61B 2017/22039; A61B 2017/22041; A61B 2017/22038; A61M 25/0026; A61M 25/003; A61M 25/0032; A61M 25/0037
See application file for complete search history.

(56) References Cited

U.S. PATENT DOCUMENTS

| | | | |
|---|---|---|---|
| 2007/0244480 A1 | 10/2007 | Suzuki | |
| 2007/0244513 A1* | 10/2007 | Weizman | A61B 10/06 606/205 |
| 2009/0005806 A1* | 1/2009 | Suzuki | A61B 17/29 606/205 |
| 2009/0124852 A1* | 5/2009 | Suzuki | A61B 18/1445 600/106 |
| 2015/0005813 A1* | 1/2015 | Maslanka | A61B 10/06 606/206 |
| 2019/0022353 A1* | 1/2019 | Khanicheh | A61M 25/0138 |

OTHER PUBLICATIONS

Invitation to Pay Additional Fees from PCT/US2018/052195 dated Dec. 13, 2018.
International Search Report and Written Opinion from PCT/US2018/052195 dated Feb. 8, 2019.

* cited by examiner

WIRE GUIDED DEVICE

CROSS REFERENCE TO RELATED APPLICATIONS

This application claims priority to and any other benefit of U.S. Provisional Patent Application No. 62/561,439, filed Sep. 21, 2017, the entire contents of which is incorporated by reference herein.

BACKGROUND

Tissue sampling may be conducted through brush cytology, fine needle aspiration (FNA), or biopsy. Endoscopic Retrograde Cholangiopancreatography (ERCP) is typically performed on patients presenting with symptoms of biliary obstruction. The symptoms include: jaundice, itching, abdominal pain, loss of appetite, fatigue, fevers and chills.

Patients with advanced or metastatic disease are not surgical candidates. In these patients, palliative biliary stent placement is the best option, with chemotherapy or radiotherapy management following a tissue diagnosis. Regardless of the type and severity of malignant or benign biliary obstruction, a tissue diagnosis is necessary to determine the best possible treatment options for the patient. Sampling results can determine cancer of the bile ducts (cholangiocarcinoma), cysts in the liver, liver cancer, pancreatic cancer, or swelling and scarring of the bile ducts (PSC or primary sclerosing cholangitis). At present, a two-tiered approach using more than one method of sampling is preferred, yet triple sampling with brush cytology, FNA and biopsy forceps has the highest sensitivity.

SUMMARY

The present subject matter describes a wire guided device, comprising: a sheath, a working assembly, comprising: a working portion configured to contact an intended tissue, a connector, connecting the working portion and the sheath, and a wire guide, disposed at and connect to the working assembly. The wire guide is configured to allow a guide wire to pass through. The wire guide is disposed at a predetermined distance from a distal end of the working assembly. The wire guide and the guide wire does not interfere an operation of the working portion.

The present subject matter further describes a wire guided device, comprising: a sheath, a working assembly, comprising: a working portion, configured to contact an intended tissue, a connector, connecting the working portion and the sheath, and a wire guide, disposed at and connect to the sheath. The wire guide is configured to allow a guide wire to pass through.

The present subject matter further describes a wire guided device, comprising: a sheath, a working assembly, comprising: a working portion, configured to contact an intended tissue, a connector, connecting the working portion and the sheath, and a wire guide, removably disposed at and connect to the connector. The wire guide is configured to allow a guide wire to pass through. The wire guide and the guide wire does not interfere an operation of the working portion. The working assembly remains same operational functions without the wire guide, beside the wire guided function.

BRIEF DESCRIPTION OF THE DRAWINGS

Features and advantages of the general inventive concepts will become apparent from the following detailed description made with reference to the accompanying drawings.

DETAILED DESCRIPTIONS OF INVENTION

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The present subject matter discloses a wire guided device 100. The wire guided device 100 may include, but not limited to, various formats of forceps, scissors, graspers, clips, cutters, and other suitable surgical devices used for endoscopic, urological, or other similar surgical procedures. The surgical devices are often used in a narrow space, such as a body cavity. The present subject matter will be described as exemplary forceps assembly 100. However, the present subject matter should not be limited to the embodiments described below.

Figure 1:
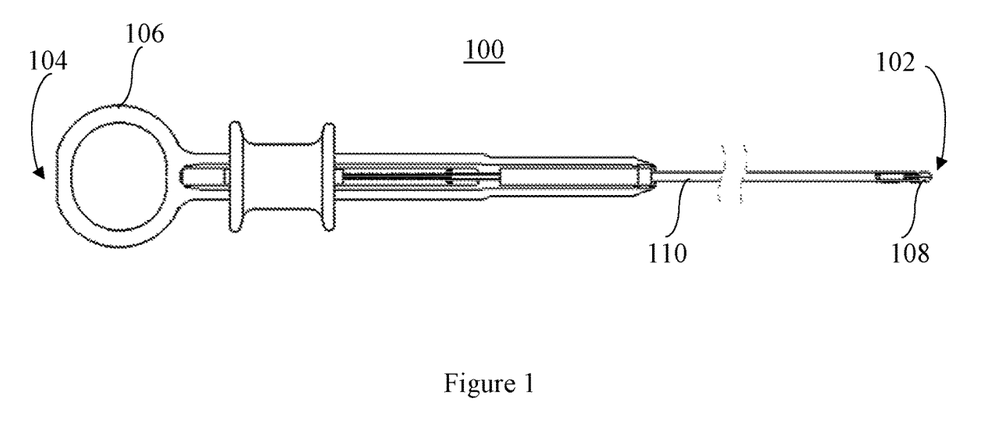
FIG. 1 is a perspective view of the forceps assembly of the present subject matter.

As shown in FIG. 1, the forceps assembly 100 has a distal end 102 and a proximal end 104. The forceps assembly comprises a handle 106 disposed at the proximal end 104, a working assembly 108 disposed at the distal end 102, and a sheath 110 disposed and connected between the handle 106 and the working assembly 108. A user is able to open or close the working assembly 108 by pushing and pulling a spindle of the handle 106. The working assembly is used to collect the sample. In some embodiments, the sheath 110 is a spring sheath.

Figure 2:
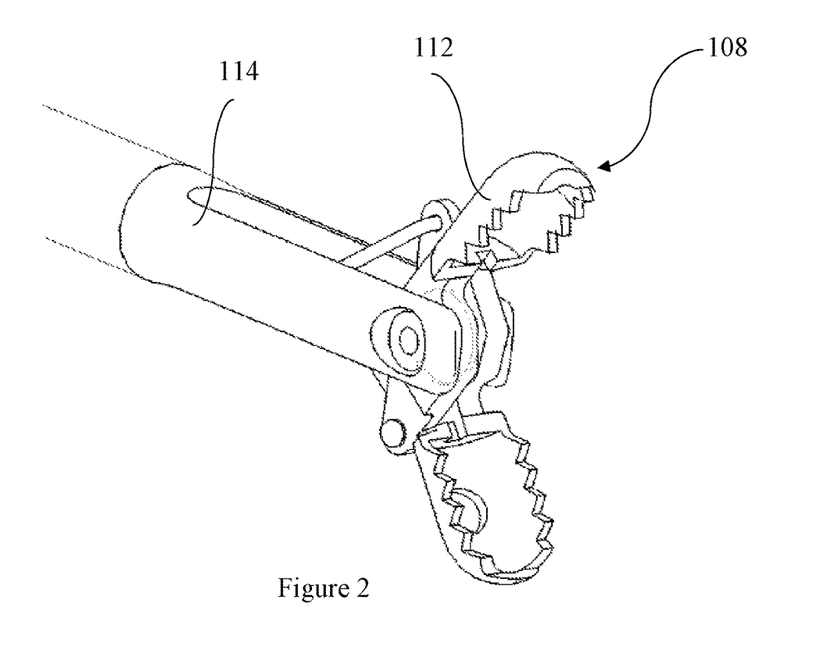
FIG. 2 is a partial view of the forceps assembly, showing the working assembly without the wire guide.

In some embodiments, for example shown in FIG. 2, the working assembly 108 comprises working portion 112 and a connector 114. The connector 114 is configured and sized to hold the working portion 112. In this embodiment of the forceps, the working portion 112 is cups 112. In some embodiments, the cups 112 have serrated edges. In some other embodiments, the cups 112 have smooth edges (not shown).

Figure 8:
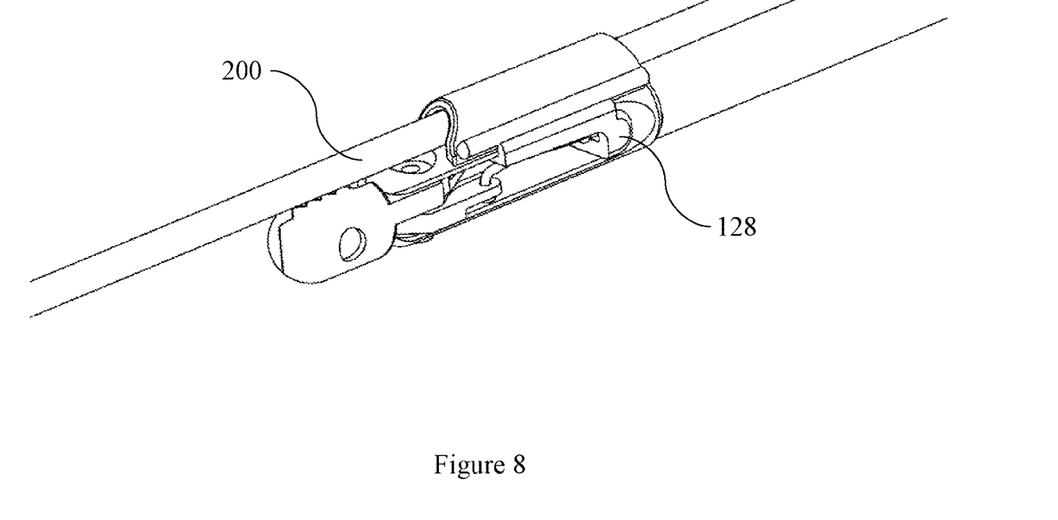
FIG. 8 is a partial view of the forceps assembly shown in FIG. 4 with the guide wire.

Some aspects of the present subject matter are to address the challenges of biliary biopsy sampling, specifically, to gain access and obtain a biopsy in the bile duct. In some embodiments, the forceps assembly 100 is used in a duodenoscope and to track along a guide wire 200 in an optimum manner as shown in FIG. 8, so that the forceps assembly 100 can reach to the same intended location of the tissue at multiple times. The forceps assembly 100 is suitable for novice and proficient physicians for clinical use and allows for consistent biopsy sampling even in the most difficult situations. The forceps assembly 100 reduces or avoids separation of the guidewire and the distal end of the forceps assembly 100. Furthermore, the forceps assembly 100 may easily traverse the elevator channel of the duodenoscope.

Figure 11:
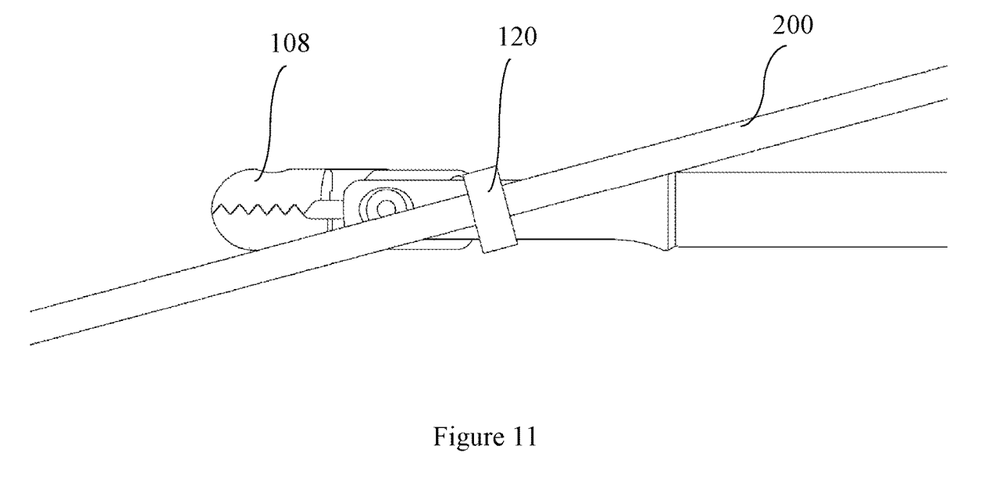
FIG. 11 is a top view of the forceps assembly with an embodiment of a nonparallel wire guide.
Figure 12:
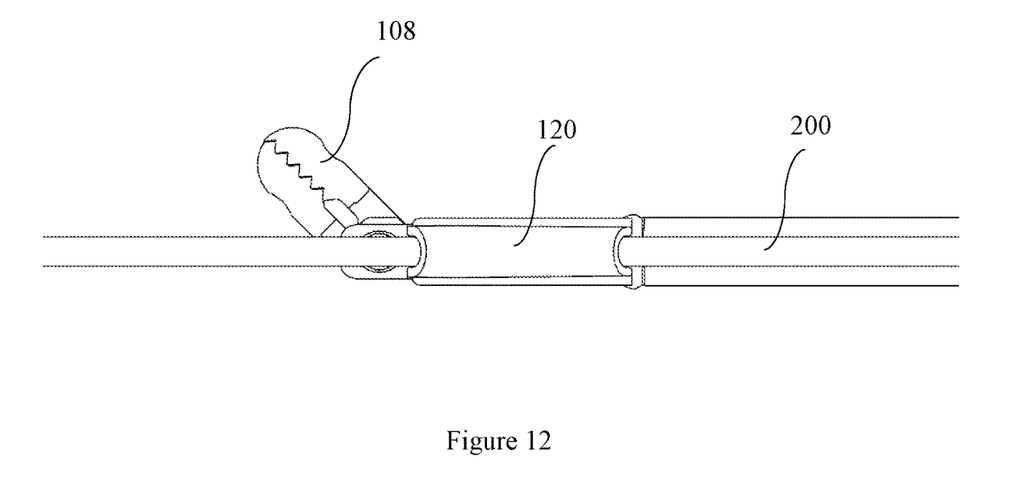
FIG. 12 is a top view of the forceps assembly with another embodiment of a nonparallel wire guide.

The forceps assembly 100 further comprises a wire guide 120. In some embodiments, the wire guide 120 is a ring. In some embodiments, the wire guide 120 is a tube. In some embodiments, the wire guide 120 is a clip. In some embodiments, the wire guide 120 is a channel. The wire guide 120 may be other suitable configurations to guide a guide wire to pass though. In some embodiments, the internal surface 122 of the wire guide 120 is configured and sized to limit the potential movement of the guide wire to be substantially parallel to the sheath 110. In some embodiments, the axis direction of the wire guide 120 is substantially parallel to the axis direction of the working assembly 108. Therefore, the potential movement of the guide wire is limited to only the axis direction of the forceps assembly 110. In some embodiments, the length of the wire guide 120 along its axis direction is from about 1 mm to more than about 30 cm. In some embodiments, such as shown in FIGS. 11 and 12, the axis direction of the wire guide 120 is not parallel to the axis direction of the working assembly 108. The nonparallel wire guide may bring some advantages under certain surgical situations. This can lead the forceps assembly to move and work in certain desired angles to the guide wire.

The wire guide 120 is configured to be disposed closer to the distal end 102 of the forceps assembly 100 than the proximal end 104 of the forceps assembly 100, to avoid the separation described above. Generally speaking, the closer to the distal end 102 of the forceps assembly 100, the less separation will occur. In some other embodiments, the wire guide 120 is disposed at the sheath 110 but still near the working assembly 108. In some embodiments, the wire guide 120 is disposed at least 3 mm from the distal end 102 of the forceps assembly 100. In some embodiments, the wire guide 120 is disposed at least 3 mm from a distal end of the connector of the working assembly 108. In some embodiments, the wire guide 120 is not disposed on the working portion 112. In some embodiments, only a predetermined length of forceps assembly 100 is configured to extend beyond the endoscope; while the wire guide 120 is disposed within the predetermined length of the forceps assembly 100. In some embodiments, a portion of the wire guide 120 is disposed within the endoscope.

No matter where the wire guide is disposed, the position of the wire guide 120 should not interfere with the movement and/or open/close of the forceps cups 112.

Figure 3:
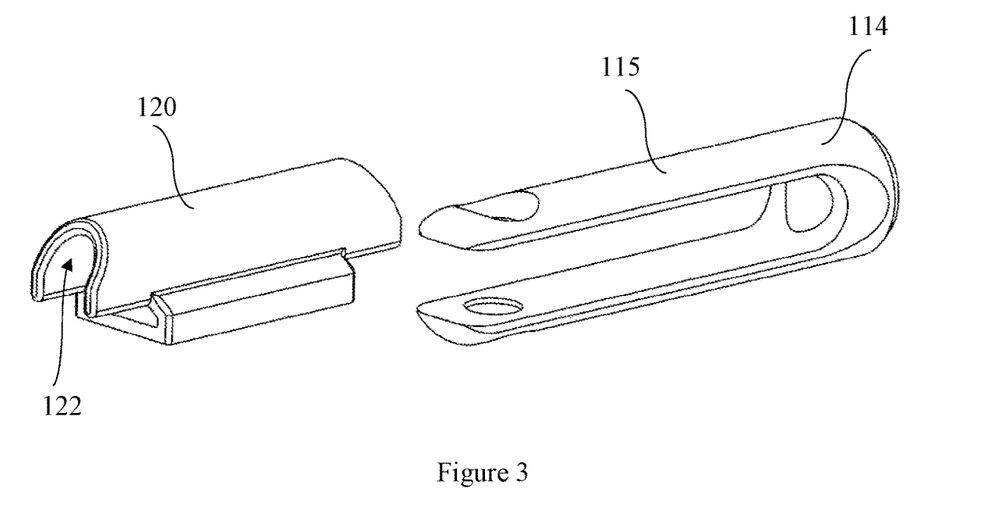
FIG. 3 is an exploded view of the connector and an embodiment of the wire guide.
Figure 4:
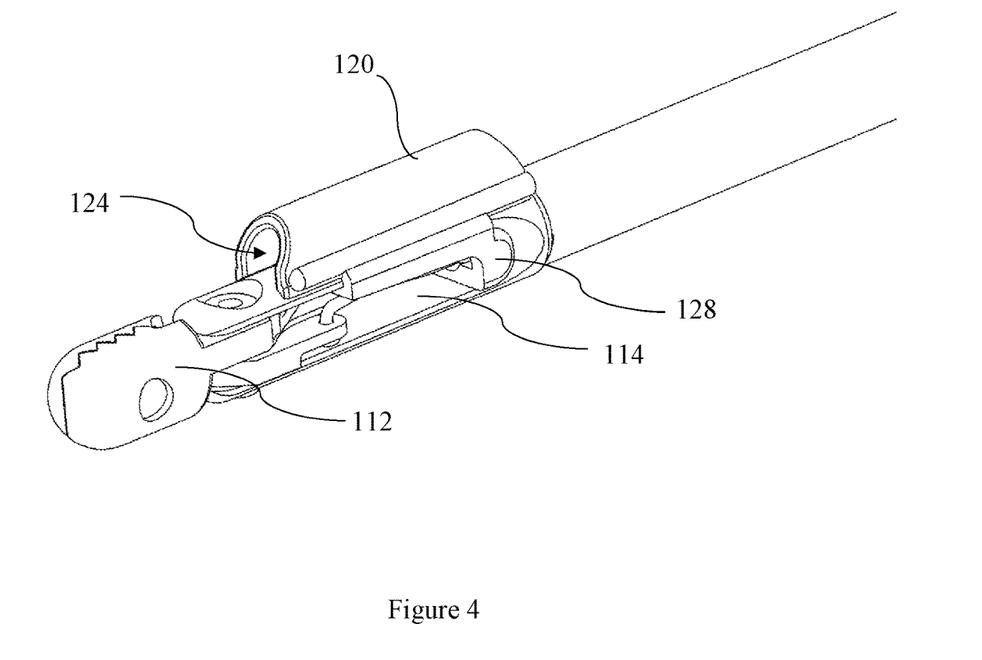
FIG. 4 is a partial view of the forceps assembly, showing the working assembly with another embodiment of the wire guide.

In embodiments as shown in FIGS. 3 and 4, the wire guide 120 is configured to slip on at least a portion of the connector 114 during the assembling process. The connector 114 comprises a fork. The at least a portion of the connector 114 is a side arm 115 of the connector 114 in this embodiment. However, a person skilled in the art should understand the wire guide 120 may slip on another portion of or the whole connector 114. At the assembled position of the wire guide 120, the other components of the working assembly 108 limit any movement of the wire guide 120 and achieve a slip-on effect. Meanwhile, the outside surface of the connector 114 and the inside surface 122 of the wire guide 120 form a channel 124 to guide the guide wire.

Figure 5A:
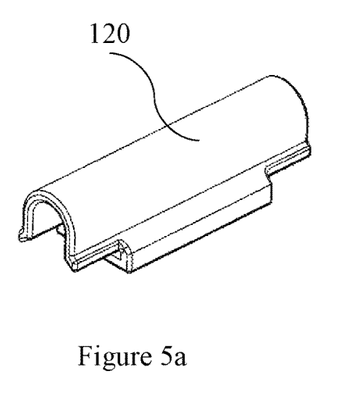
FIG. 5a-5c show various views of a third embodiment of the wire guide.
Figure 5B:
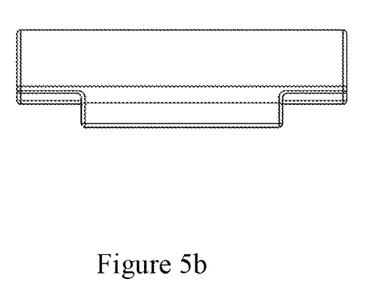
Figure 5C:
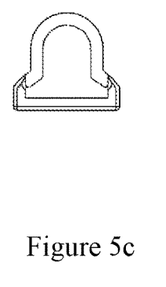
Figure 6A:
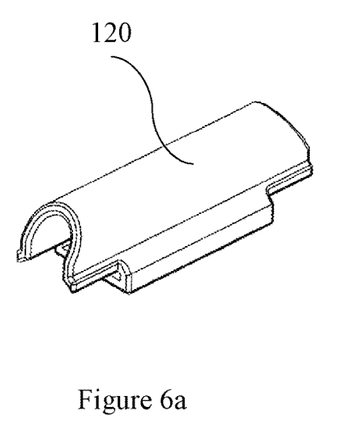
FIG. 6a-6c show various views of the wire guide shown in FIG. 3.
Figure 6B:
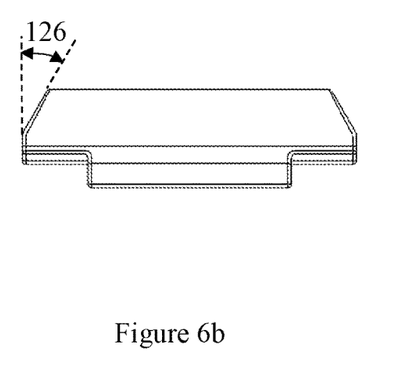
Figure 6C:
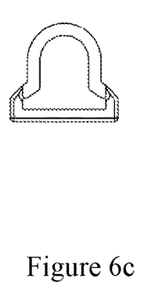

In some embodiments, the wire guide 120 is removable. One of the benefits of the wire guide 120 shown in FIGS. 3, 5, and 6 is that the connector 114 does not need to be altered. Therefore, the connector 114 can be used the same design as the regular forceps assemblies.

In some embodiments, such as shown in FIGS. 4 and 8-10, the wire guide further comprises a stopper 128. The stopper 128 limits the movement of the wire guide 120 in the proximal direction. In some embodiments, at least a portion of the stopper 128 inserts into a working channel 132 of the connector 114. In some embodiments, at least a portion of the stopper 128 exactly fits into the working channel 132.

Figure 9:
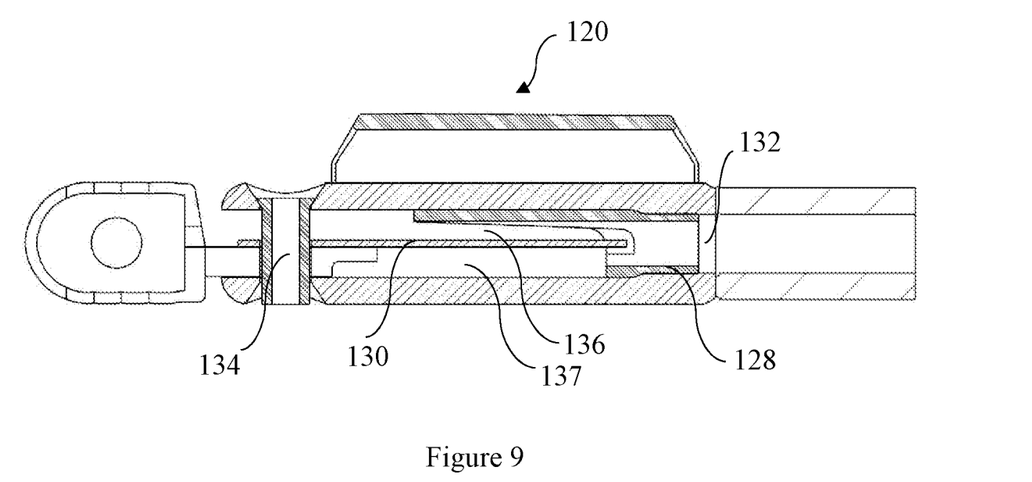
FIG. 9 is a cross sectional view of the forceps assembly shown in FIG. 4 without driving cables.
Figure 10:
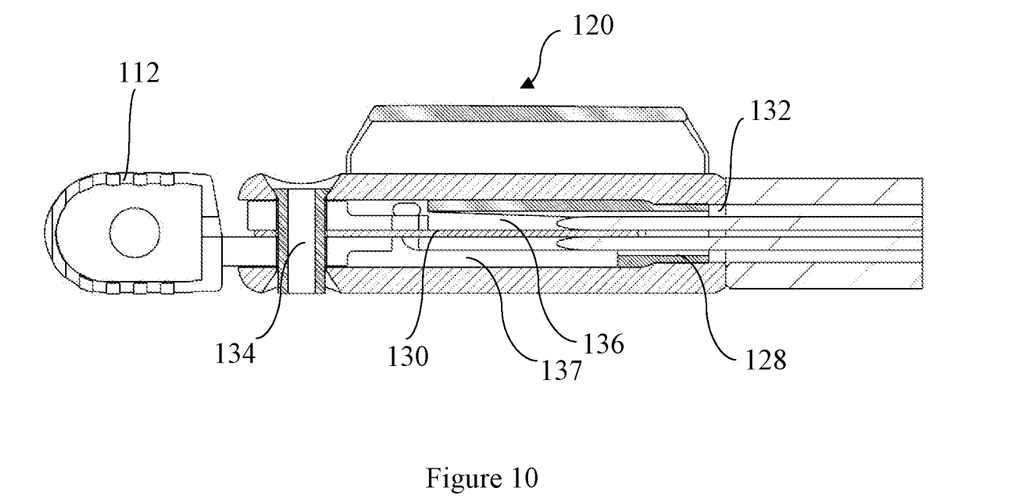
FIG. 10 is a cross sectional view of the forceps assembly shown in FIG. 4 with driving cables.
Figure 13:
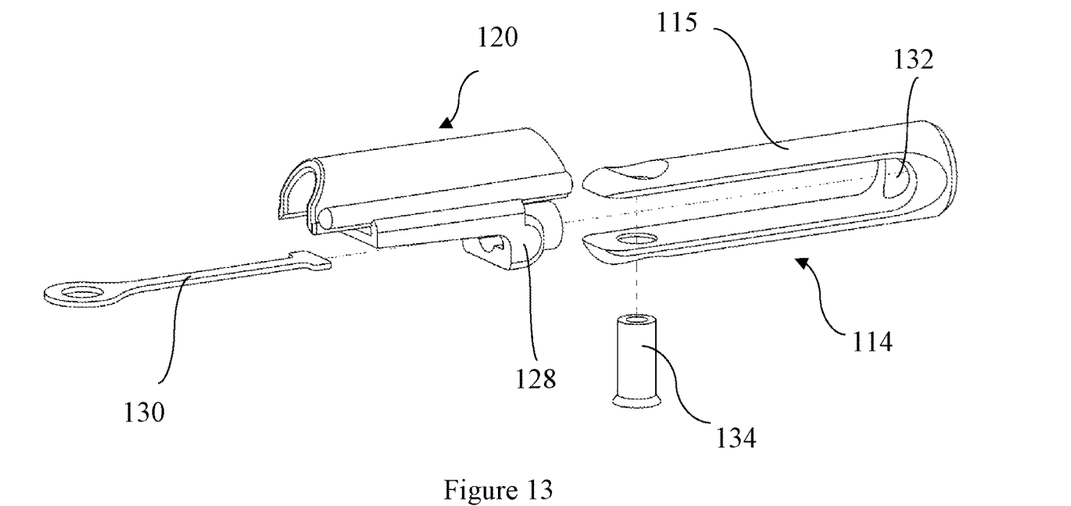
FIG. 13 is an exploded view of the connector and the wire guide shown in FIG. 4 with a spacer.

FIG. 6 shows another exemplary wire guide 120 of FIG. 3. FIG. 5 shows yet another exemplary wire guide 120, and with angled and radius features. The angled features and/or radius at both or either end of the wire guide may reduce the possibility of the wire guide being caught in the elevator while traversing through the duodenoscope during insertion and extraction. The angled end 126 of the wire guide 120 is up to about 60 degrees. In one embodiment, the angle 126 is about 30 degrees. In one embodiment, the length of the wire guide is about 7 mm. The height of the wire guide is about 2 mm. In one embodiment, the wire guide 120 allows a standard guide wire with a diameter of up to about 0.035 inches to pass through. A person skilled in the art should understand that the angle, the length, and the height of the wire guide and the diameter of the guide wire are not limited to the above described numbers. Any angle, length, height of the wire guide, or diameter of the guide wire suitable for endoscopic use can be used here In some embodiments, such as shown in FIGS. 9, 10, and 13 the forceps assembly 100 further comprises a spacer 130. The spacer 130 is linked to the pivot point 134 of the forceps assembly 100. The spacer 130 separates the two moving arms 136, 137 of the forceps assembly 108 and prevents the two moving arms 136, 137 from dislocating. A proximal end of the spacer 130 is insert into a recess of the stopper 128, so as to prevent the wire guide 120 from moving towards the distal direction.

Figure 7:
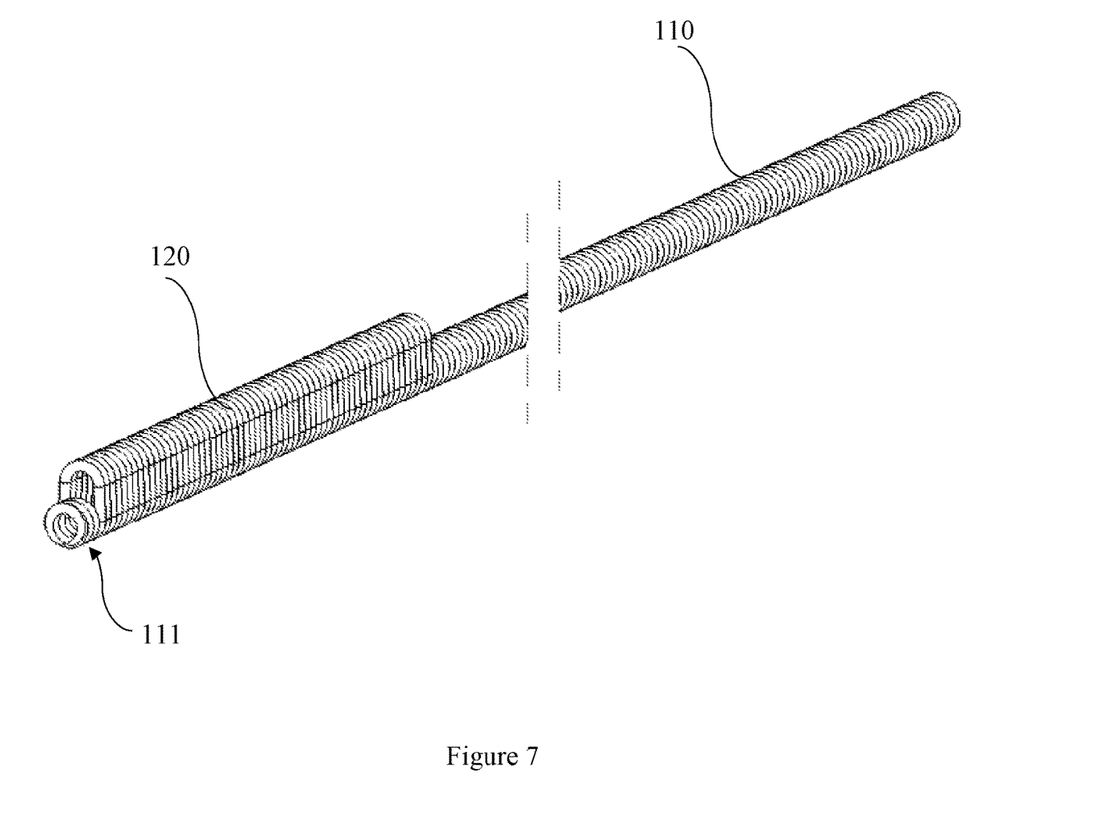
FIG. 7 is a perspective view of a fourth embodiment of wire guide with the sheath.

Another embodiment of the present subject matter is the wire guide 120 deposed on the sheath 110, as shown in FIG. 7. Instead of on the connector 114, a wire guide 120 is disposed on a spring sheath 110. The wire guide 120 is attached to the outside wall of the sheath 110. In some embodiments, the wire guide 120 is at or near the distal end 111 of the sheath 110. In some embodiments, the inside surface of the wire guide 120 alone provides a geometry which is configured to guide and control the forceps assembly 100 along the guide wire. In some embodiments, the outside surface of the sheath 110 and the inside surface of the wire guide 120 together provide a geometry which is configured to guide and control the forceps assembly 100 along the guide wire. The length of the wire guide 120 may range up to 30 cm. In this embodiment, the wire guide is made of the same material of the spring sheath 110.

The wire guide 120 may be welded, adhered, overmolded, or otherwise connected to the other components of the forceps assembly 100. In some embodiments, the wire guide 120 and one or more components of the forceps assembly 100 are made in one piece. In some embodiments, the wire guide 120 is compassed with the spring sheath during the winding of the spring as shown in FIG. 7.

The wire guide 120 may be made of metal, plastic material, polymer material, or any other suitable material, or any combinations thereof. In some embodiments, the wire guide 120 is made of the same material as other components of the wire guided device. In some embodiments, the wire guide 120 is made of the different material as other components of the wire guided device. In some embodiments, the internal surface of the wire guide 120 is coated. In some embodiments, the internal surface of the wire guide 120 is coated by a hydrophilic coating, such as hydrophilic polymer.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

The invention claimed is:

1. A wire guided device, comprising:
   a sheath,
   a working assembly, comprising:
   a working portion, configured to contact an intended tissue,
   a connector, connecting the working portion and the sheath, and
   a wire guide, disposed at and connected to the working assembly,
   wherein the wire guide is configured to allow a guide wire to pass through, wherein the wire guide is disposed at a predetermined distance from a distal end of the working assembly, wherein the wire guide and the guide wire do not interfere with an operation of the working portion,
   wherein the wire guided device is a forceps assembly comprising a spacer, wherein the spacer is linked to a pivot point of the forceps assembly and separates two moving arms of the forceps assembly to prevent the two moving arms from a dislocation, wherein the wire guide further comprises a stopper, wherein a proximal end of the spacer is inserted into a recess of the stopper, so as to prevent the wire guide from moving towards the distal end.

2. The wire guided device of claim 1, wherein the wire guide is a channel.

3. The wire guided device of claim 1, wherein an internal surface of the wire guide is configured and sized to limit potential movements of the guide wire to be substantially parallel to an axis direction of the working assembly.

4. The wire guided device of claim 3, wherein an axis direction of the wire guide is substantially parallel to an axis direction of the working assembly.

5. The wire guided device of claim 1, wherein an internal surface of the wire guide is configured and sized to limit potential movements of the guide wire to be nonparallel to an axis direction of the working assembly.

6. The wire guided device of claim 5, wherein an axis direction of the wire guide is nonparallel to an axis direction of the working assembly.

7. The wire guided device of claim 1, wherein a length of the wire guide along its axis direction is from 1 mm to 30 cm.

8. The wire guided device of claim 1, wherein the wire guide is disposed closer to a distal end of the working assembly than a proximal end of the working assembly.

9. The wire guided device of claim 1, wherein the wire guide is disposed at least 3 mm from a distal end of the working assembly.

10. The wire guided device of claim 1, wherein the wire guide is disposed at least 3 mm from a distal end of the connector.

11. The wire guided device of claim 1, wherein the wire guide removably engage on at least a portion of the connector.

12. The wire guided device of claim 11, wherein the at least a portion of the connector is a side arm.

13. The wire guided device of claim 11, wherein the working assembly limits any movement of the wire guide once the wire guide engages on the connector.

14. The wire guided device of claim 1, wherein at least a portion of the stopper inserts into a working channel of the connector.

15. The wire guided device of claim 1, wherein the wire guide comprises an angled end.

16. The wire guided device of claim 1, wherein the wire guide is welded, adhered, or over-molded to the working portion or the connector.

* * * * *